United States Patent [19]
Burns et al.

[11] Patent Number: 5,969,211
[45] Date of Patent: Oct. 19, 1999

[54] PANTROPIC RETROVIRAL VECTORS FOR GENE TRANSFER IN MOLLUSKS

[75] Inventors: Jane C. Burns, La Jolla, Calif.; Thomas T. Chen, Storrs, Conn.

[73] Assignees: Ther Regents of The University of California, Oakland, Calif.; The University of Conneticut, Farmington, Conn.

[21] Appl. No.: 08/844,530

[22] Filed: Apr. 18, 1997

Related U.S. Application Data

[60] Provisional application No. 60/016,253, Apr. 19, 1996.
[51] Int. Cl.[6] .............................. C12N 5/00; C12N 15/00
[52] U.S. Cl. .................................. 800/23; 800/8; 800/13
[58] Field of Search ............................... 800/2, DIG. 1–4, 800/23, 8, 13; 435/172.3

[56] References Cited

U.S. PATENT DOCUMENTS 5,675,061 10/1997 Powers et al. ............................... 800/8

OTHER PUBLICATIONS

Chen et al. Production of transgenic dwarf surfclams, *Mulinia lateralis*, with pantropic retroviral vectors. Appeared in the Journal of Shellfish Research. Presented at the Annual Meeting of the National Shellfisheries Association, Baltimore, MD., Downl, Apr. 18, 1996.

*Primary Examiner*—Brian R. Stanton
*Assistant Examiner*—Deborah J. R. Clark
*Attorney, Agent, or Firm*—Knobbe, Martens, Olson & Bear, LLP

[57] ABSTRACT

A method for introducing foreign nucleic acid sequences into marine mollusks. A pantropic retroviral vector containing a foreign gene sequence is introduced into fertilized mollusk embryos by electroporation. The gene sequence becomes integrated into the host DNA and encodes a functional protein product. This method has implications in the introduction of disease-resistance and growth-accelerating genes into mollusks.

15 Claims, 2 Drawing Sheets

PANTROPIC RETROVIRAL VECTORS FOR GENE TRANSFER IN MOLLUSKS

This application claims the benefit of priority to U.S. provisional application Ser. No. 60/016,253, filed Apr. 19, 1996.

GOVERNMENT INTEREST IN INVENTION

Certain aspects of the present invention were made with government support under SeaGrant (division of NOAA) and National Science Foundation Grant No. IBN 937132. The government has certain rights in these aspects of the invention.

FIELD OF THE INVENTION

The present invention relates to the transfer of DNA into organisms. More specifically, the invention relates to the stable transfer of genes into the DNA of marine mollusks using pseudotyped pantropic retroviral vectors.

Background of the Invention The stable transfer of heterologous genes into organisms has been used to address a variety of fundamental questions in species ranging from Drosophila to mice (Palmiter et al., Ann. Rev. Genet., 20:465–499,1986). For example, the work of the present inventors disclosed in allowed U.S. patent application Ser. No. 08/104,804 and the corresponding published International Application No. PCT/US94/06272 discloses the use of VSV-G Pseudotyped Retroviral Vectors in the transfer of genes into a variety of different mammalian and non-mammalian organisms. However, heretofore, it has not yet been possible to stably transfer heterologous genes into the germline of marine mollusks, whereby $F_1$ generation mollusks retain and express the heterologous genes.

Natural mollusk populations are threatened by disease and environmental stress (Houde et al., Estuaries, 16:161–167, 1993). Candidate genes for improving disease resistance and hardiness have been identified in commercially important bivalve mollusks. Such genes encode, for example, invertebrate antibacterial proteins such as insect cecropins, defensins, magainins, diptericins and attacins which are described by Hoffman et al. Phylogenetic Perspectives in Immunity: The Insect Host Defense, R. G. Landers Co, Austin, Tex., (1994) and Cociancich et al. Parasitology Today, 10:132–139 (1994), the entire contents of which are hereby incorporated by reference. These genes will confer resistance to various pathogens which plague mollusks. Several cecropin genes have been characterized in various insect species. Boman et al., Eur. J. Biochem., 201:23–31 (1991), the entire disclosure of which is hereby incorporated by reference. However, because no method currently exists for genetic manipulation of marine mollusk species, it has not yet been possible to successfully transfer these genes to stably protect populations of mollusks. The absence of transformed cell lines has hampered the development of methods for transfer of genes into mollusks.

The dwarf surfclam, Mulinia lateralis (family Mactridae) is a useful model species for shellfish genetic studies (Guo et al., Genetics, 138:119–126, 1994). Its short generation time (2–3 months), ease of laboratory cultivation, small space requirements, reasonable longevity (2 years), high fecundity (0.5–2 million eggs per spawning), and ease of in vitro fertilization make it an ideal bivalve model for gene transfer studies. Since males and females are easily distinguished in the mature clam, it is possible to separate them and make specific crosses. Although a large number of eggs are produced, the small size (50 mm) and opacity of the oocyte make the introduction of foreign DNA by microinjection technically difficult.

Infection of cells with retroviral vectors results from specific interaction of the viral envelope glycoprotein with cellular receptors, defining the host range and determining the efficiency of infection. Pantropic retroviral vectors containing the genome of Moloney murine leukemia virus (MoMLV) and the rhabdovirus vesicular stomatitis virus (VSV) G envelope glycoprotein have been used to infect fish, and newt cell lines (Burns et al., Proc. Natl. Acad. Sci. U.S.A., 90:8033–8037, 1993; Burns et al., Dev. Biol., 165:285–289, 1994). Virions having the genome of MoMLV and the G envelope protein of VSV G have been termed "pseudotypes". In vivo infection of zebrafish lines, with the creation of transgenic animals, has also been reported (Lin et al., Science, 265:666–669, 1994). However, the microinjection technique used to create these transgenic lines requires great technical precision and is labor-intensive. These retroviral vectors exhibit a broad host range of infectivity due to the VSV-G protein.

Thus, there is a need for an effective gene transfer method which will allow the introduction of desirable genes into the germline DNA of marine mollusks. The present invention satisfies this need.

SUMMARY OF THE INVENTION

One embodiment of the present invention is a method for introducing foreign DNA into the germline of a marine mollusk, comprising the steps of:

inserting the foreign DNA into a retroviral vector;

forming a pantropic retroviral pseudotype with the foreign RNA-containing retroviral vector; and infecting mollusk embryos with said retroviral pseudotype.

Advantageously, the DNA can encode a growth-accelerating protein or a protein conferring resistance to pathogens. In a preferred embodiment, the protein is a growth hormone, insulin-like growth factor, cecropin, defensin, attacin, diptericin or magainin. Preferably, the marine mollusk is a clam. Alternatively, the marine mollusk can be an oyster, mussel, scallop or abalone. In certain embodiments, the retroviral vector is LSRNL or Geo4.8. Preferably, the infecting step is facilitated by electroporation. Alternatively, the infecting step is performed by dechorionation or microinjection.

The present invention also provides a marine mollusk containing foreign DNA inserted into its germline, the DNA contained within a provirus. Preferably, the DNA encodes an invertebrate defense protein. Advantageously, the defense protein can be a protein which confers disease-resistance, such as cecropin, defensin, attacin, diptericin or magainin.

DETAILED DESCRIPTION OF THE PREFERRED EMBODIMENTS

The present invention provides a method for transferring foreign DNA sequences into marine mollusks using pseudotyped retroviral vectors containing the genome of a retrovirus and the envelope glycoprotein of VSV (i.e. VSV-G protein) which confers broad host range. As used herein, the term "pantropic" indicates a retroviral pseudotype in which the envelope glycoprotein is VSV-G; and the term "provirus" indicates the DNA form of the virus. The substitution of the VSV-G glycoprotein for the amphotropic retroviral envelope protein confers upon the resultant pseudotyped vector particles a broadened host range and the ability to be concentrated to high titer by ultracentrifugation. These pseudotyped pantropic retroviral vectors can infect many mammalian and non-mammalian species. Advantageously, because these retroviral vectors are replication-deficient, they can be safely used following guidelines for recombinant DNA techniques (BSL2).

Powers et al. (*Mol. Mar. Biol. Biotechnol.*, 4:369–375, December 1995) introduced the β-galactosidase gene into fertilized abalone eggs by electroporation and determined that the foreign gene was retained in the genome of juvenile organisms as head-to-tail concatemers integrated in the abalone genome. However, the $F_1$ generation did not retain the foreign gene. Despite the lack of previous success in transfecting marine mollusks, we have unexpectedly discovered that pantropic pseudotyped retroviral vectors provide a useful method for the stable introduction of foreign nucleic acid into marine mollusks. The present invention is believed to be the first successful transfer of genes into a marine mollusk, whereby the gene is stably retained and expressed in $F_1$ and subsequent generation mollusks.

The present invention is described hereinbelow in specific detail in connection with the transfection of dwarf surfclams using electroporation techniques. The dwarf surfclam system described is meant to be illustrative of the invention in view of its acceptance in the art as a model system for studying marine mollusk genetics. Accordingly, the disclosure relating to this specific species and gene transfer technique is not intended to limit the present invention. Thus, the introduction of foreign nucleic acid sequences into other marine mollusks is also within the scope of the invention. Such mollusks include oysters, mussels, clams, scallops and abalone. In a preferred embodiment, foreign DNA is introduced by electroporation of fertilized eggs. Other methods of DNA introduction contemplated for use in the invention include dechorionation and microinjection. Low voltage electroporation transiently disrupts the vitelline membrane allowing direct contact of the virus particles with the embryo surface, but does not compromise the integrity of the embryo. The electroporation conditions can be optimized for a particular mollusk species by one of ordinary skill in the art without undue experimentation.

Invertebrate defense genes which confer resistance to various pathogens may be transferred into the mollusk germline. Such genes include the cecropins, magainins, diptericins, defensins and attacins (Hoffman et al. *Phylogenetic Perspectives in Immunity: The Insect Host Defense*, R. G. Landers Co, Austin, Tex., 1994; Cociancich et al. *Parasitology Today*, 10:132–139, 1994). This will improve the resistance of mollusk populations to disease. Genes encoding growth regulating hormones will accelerate mollusk growth and result in larger animals. For example, Paynter et al. (*Biol. Bull.*, 181:459–462, 1991), the contents of which are hereby incorporated by reference, treated oysters with recombinant trout growth hormone. The growth hormone-treated oysters were significantly larger than control oysters. The introduction of additional gene copies of, for example, growth-accelerating hormones into various mollusk species will accelerate growth of these organisms, resulting in larger mollusks for harvesting and consumption. Because the exogenous growth-accelerating genes are under control of a constitutive promoter, growth will be greatly accelerated due to the inability of endogenous transcription control factors to down regulate expression of the growth hormone gene.

The basic protocol for infection of surfclams in our model system was performed without the need to resort to highly specialized mechanical or physical techniques. Newly-fertilized dwarf surfclam embryos were incubated with culture supernatant containing pantropic retrovirus containing the bacterial gene encoding β-galactosidase. These embryos were subjected to electroporation to facilitate virus attachment to the cell surface. Embryos tested positive for the provirus 2–3 days after infection. 30–40% of the gamete pools (eggs and sperm) collected from individuals allowed to mature to adulthood ($P_1$ individuals) contained the provirus. After outbreeding of this $P_1$ generation, the resulting $F_1$ generation contained a single, integrated copy of the transgene in 25–30% of the $F_1$ animals. Expression of the β-galactosidase transgene encoded by the provirus was detected in transgenic but not control animals. This was the first demonstration of a transgenic mollusk in which there is absolute documentation of transgene integration in the $F_1$ generation.

In a preferred embodiment, the polycation polybrene can also be used to facilitate virus attachment to the embryo surface. The use of other polycations including, for example, protamine sulfate and poly-L-lysine is also within the scope of the invention.

The envelope protein of pantropic retroviral vectors interacts with phospholipids in the plasma membrane to mediate virus attachment. The absence of a requirement for a specific protein receptor on the cell surface confers an extremely broad host cell range upon these vectors. In addition, the stability of the envelope protein allows concentration of vector particles to high titer by ultracentrifugation as described in allowed copending U.S. application Ser. No. 08/104,804 which is scheduled to issue as U.S. Pat. No. 5,512,421 on Apr. 30, 1996, the entire contents of which are hereby incorporated by reference. These retroviral vectors can accommodate up to about 10 kilobases of heterologous cDNA and promoter sequences, are easy and inexpensive to produce, and mediate stable insertion of the retroviral genome carrying transgenes into the host cell genome. No other system exists for the efficient and stable introduction of foreign DNA into the germline of mollusk species.

Any pantropic retroviral vector is contemplated for use in the invention, including LSRNL(VSV-G), LSPONL(VSV-G) and LZRNL(VSV-G). pLSPONL and pLZRNL are described by Yee et al. (*Proc. Natl. Acad. Sci. U.S.A.*, 91:9564–9568, 1994). The VSV-G pseudotypes corresponding to these constructs can be constructed as described in Example 2 for the pLSRNL(VSV-G) pseudotype. The use of other rhabdovirus envelope glycoproteins is also contemplated in the generation of pseudotyped pantropic retroviral vectors for use in the invention. MoMLV-based retroviral vectors are particularly preferred. For production of retroviral vector particles, the nucleic acid of the vector particles of the present invention can be used to transfect a suitable packaging cell line. Typically, the suitable cell line expresses the gag and pol genes required for retroviral replication. In a preferred embodiment, the vector particle contains DNA encoding a drug resistance gene (i.e. neomycin resistance). Cells containing the vector particles are selected by incubation in the corresponding drug (i.e. G418). The resistant cells are expanded and infected with a plasmid containing a gene which encodes an envelope glycoprotein which confers broad host range upon the pseudotyped retroviral vector. The vector particles are released into the supernatant from the transfected cells, titered using an appropriate cell line, and used to infect mollusk embryos by electroporation.

The gene encoding VSV-G can be incorporated within the nucleic acid of the vector particle. Alternatively, the gene for this envelope protein could be expressed from a third fragment of nucleic acid or from the genome of the producer cell. In a preferred embodiment, the nucleic acid within the vector particle is integrated into the cellular genome of the cell infected by the vector particle and the envelope gene is located on a different fragment of nucleic acid than the nucleic acid that is vector particle genome. Thus, in this preferred embodiment, the membrane-associated protein will not be produced by the vector particle infected cells containing the integrated nucleic acid from the vector particle.

The following examples are illustrative of various steps for carrying out the present invention. These examples are provided for illustration purposes only and are not intended to limit the invention. Example 1 describes one embodiment for preparation of embryos for electroporation.

EXAMPLE 1

Preparation of Surfclam Embryos

Dwarf surfclams, *Mulinia lateralis,* were obtained from stocks held at the Haskin Shellfish Research Laboratory (Port Norris, N.J.). Eggs and sperm were prepared from sacrificed ripe males and females and were combined for 30–40 minutes to allow fertilization, completion of meiosis and several cell divisions. The fertilized eggs were collected by brief centrifugation (6,400 rpm, 2–3 sec) and transferred to an electroporation cuvette.

As stated above, pantropic pseudotyped retroviral vectors can be prepared in a variety of ways. One exemplary method for preparing these vectors is described below in Example 2.

EXAMPLE 2

Preparation of Pseudotyped Pantropic Retroviral Vectors

Figure 1:
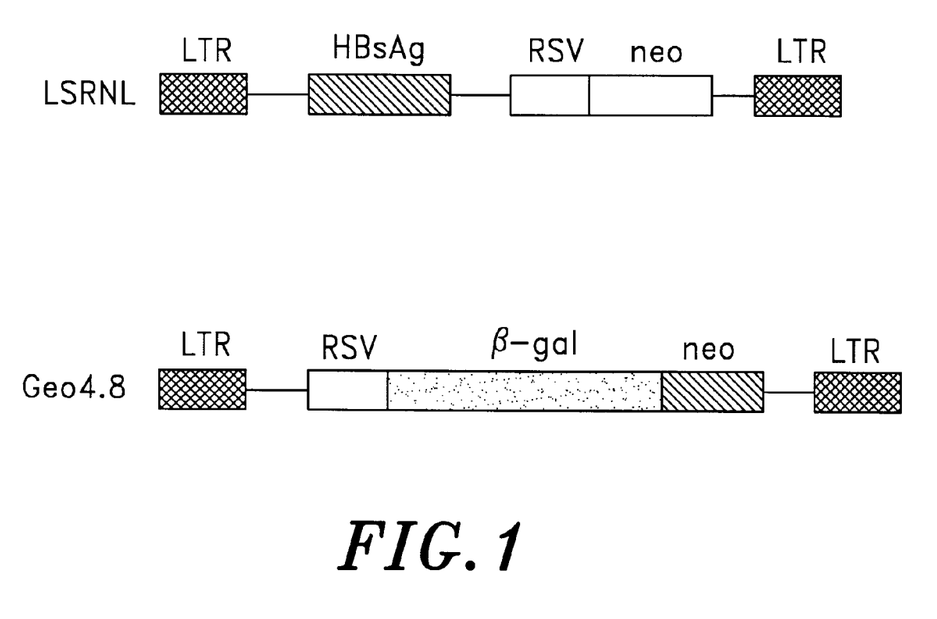
FIG. 1 is a schematic diagram showing the genomic organization of the pLSRNL and pGeo4.8 pantropic retroviral vectors. LTR, Moloney murine leukemia virus long terminal repeat; HBsAg, Hepatitis B surface antigen; RSV, Rous sarcoma virus LTR; Neo, neomycin resistance gene; β-gal, gene encoding β-galactosidase.

The pseudotyped pantropic retroviral vector LSRNL (VSV-G), in which the MoMLV LTR (L) drives expression of HBsAg (S) and the RSV LTR(R) drives expression of neomycin phosphotransferase (N), was prepared as described by Burns et al. (*Proc. Natl. Acad. Sci. U.S.A.,* 90:8033–8037, 1993; *Dev. Biol.,* 165:285–289, 1994). Briefly, the amphotropic packaging cell line PA317 (ATCC CRL 9078), which expresses retroviral gag, pol and env, was transfected with pLSRNL (Miyanohara et al., *New Biologist,* 4:261–267, 1992; FIG. 1). After 48 hours, cell culture supernatant containing amphotropic vector particles was harvested and used to infect the human adenovirus 5-transformed embryonal kidney packaging cell line 293 (ATCC CRL 1573) containing the MoMLV gag and pol genes. Cell clones containing LSRNL were selected by culturing in the presence of the antibiotic G418. Neomycin-resistant clones were expanded. The 293 cells assemble vector particles; however, theses particles are noninfectious because they lack a viral envelope protein.

The LSRNL-infected 293 cells (producer cells) were transfected by calcium phosphate coprecipitation (Graham et al., 1973) with 20 $\mu$g pHCMV-G (ATCC 75497) which expresses VSV-G from the human cytomegalovirus promoter. The culture medium was replaced with fresh medium 8 hours after transfection and the pseudotyped virus was collected between 24 and 96 hours post-transfection. The titer of the virus was determined on rat 208F fibroblasts (Emi et al., *J. Virol.,* 65:1202–1207, 1991).

The RSV-neomycin phosphotransferase-$\beta$-galactosidase construct geo is described by Friedrich et al. (*Genes Dev.* 5:1518–1528,1991). In this construct, expression of $\beta$-galactosidase and neomycin phosphotransferase is driven by the internal RSV promoter, not the MoMLV LTRs. Geo4.8(VSV-G) pseudotyped pantropic retroviral vectors were generated as described for LSRNL(VSV-G).

To determine whether the pantropic LSRNL(VSV-G) retroviral vector could infect, uncoat and reverse transcribe its genome in dwarf surfclam embryos, fertilized embryos were subjected to electroporation as described below in Example 3.

EXAMPLE 3

Electroporation of Surfclam Embryos

Electroporation was performed in a Baekon model 2000 electroporation apparatus (Baekon Co., Calif.). Conditions for electroporation were standardized using approximately 5,000–50,000 eggs (one hour post-fertilization) in 250 $\mu$l containing either equal volumes of UV-irradiated sea water (25 ppt, pH 7.25–8.25) and DMEM/10% fetal calf serum (FCS) plus $1 \times 10^4$ cfu LSRNL(VSV-G), or 2:1 sea water:virus medium. Polybrene (1 mg/ml final concentration, Sigma) was included in all infections. Control electroporations were performed with embryos in 1:1 sea water:DMEM/10% FCS. The settings on the apparatus were: voltage=700 volts; pulse frequency=$2^6$ pulses/cycle; burst time=0.4 S; cycle number=5; pulse width=160 mS; and distance of electrode from surface of buffer=1 mm. Voltage was varied from 500–700 volts to determine the optimal electroporation amplitude for retroviral penetration of the vitelline membrane. Following electroporation, embryos were incubated 0.5–1 h in the virus-containing solution, rinsed in sterile sea water and transferred to incubation buckets.

Feeding was initiated 24 h post-fertilization (post-trochophore stage) with *Isochrysis galbana* for four days. Larvae were subsequently fed a mixture of *Isochrysis galbana* and *Chaetoceros calcitrans* as previously described (Calabrese, *Proc. Natl. Shellfisheries Assoc.,* 59:65–66, 1969).

Approximately 3–5% of embryos in the infected and control groups survived to adulthood. Because survival to adulthood in undisturbed spawns is approximately 10–15%, electroporation was associated with decreased embryo survival. However, no excess mortality was observed in the group exposed to the pantropic vector. Pooled gametes (about 8,000 oocytes or 40,000 sperm) were harvested 150 days after exposure to the provirus from 53 randomly selected $P_1$ individuals: 24 which had been exposed to the 1:1 ratio of virus-containing medium to sea water and 29 which had been exposed to the 2:1 ratio.

Gamete DNA was extracted and subjected to polymerase chain reaction (PCR) amplification for detection of the neo proviral-specific gene as described in the following example.

EXAMPLE 4

DNA Extraction and PCR Amplification

Pooled gametes from $P_1$ animals were incubated in 20 $\mu$l digestion buffer containing 0.05 mg/ml Proteinase K, 1.7 mM sodium dodecyl sulfate (SDS) and 20 mM dithiothreitol (DTT) for 2 hours at 55° C., followed by incubation for 20 min at 85° C. To amplify a 349 base pair DNA fragment of the neo gene, 2–4 μl supernatant was diluted to 40 μl with PCR buffer (10 mM Tris-HCl, pH 8.3, 50 mM KCl, 0.01% gelatin) containing 0.2 mM dNTPs, 1.5 mM MgCl$_2$ and 0.25 μM of each primer: 5'-GCATTGCATCAGCCATGA-3' (SEQ ID NO:1) and 5'-GATGGATTGCACGCAGG-TTC-3' (SEQ ID NO: 2). Samples were heated to 97° C. for 8 min, cooled to 75° C. for 15 min, followed by addition of 1.25 units Taq DNA polymerase (Promega, Madison, Wis.) diluted in 10 ml PCR buffer to each tube. PCR parameters were as follows: denaturation for 1.5 min at 94° C., annealing for 2 min at 62° C. and synthesis at 72° C. for 40 cycles. The reaction was terminated with a 7 min extension at 72° C. Samples were analyzed by electrophoresis on a 2% agarose gel, transfer to a nylon membrane, and hybridization to a $^{32}$P-labeled neo cDNA probe. Of the F$_1$ gamete pools, 8/24 (33.3%) and 7/29 (24.1%) contained the neo transgene. Thus, approximately one-third on the electroporated, surviving embryos exhibited retroviral infection of their gametes.

To test for retroviral integration and gene expression, surfclam embryos were infected with the pantropic vector pGeo4.8 (FIG. 1) as described below.

EXAMPLE 5

Retroviral Integration and Gene Expression

Approximately 5,000–50,000 embryos were infected at a ratio of sea water to pGeo4.8-containing medium of 1:1. Gametes were harvested from 22 potentially germline transgenic P$_1$ surfclams, and 3/22 (13.6%) tested positive by PCR for the neo transgene. The 3 P$_1$ surfclams (1 male, 2 females) from which the positive gamete pools were derived were crossed with wild type, uninfected surfclams and the F$_1$ progeny screened by DNA dot blot hybridization for the β-galactosidase transgene. Briefly, 20 μg genomic clam DNA was dissolved in 194 μl TE buffer and denatured in 0.1 volume 10 N NaOH at 65° C. for 1 hour. Samples were neutralized with 0.2 volume 6 M ammonium acetate and spotted onto a moistened nitrocellulose membrane in a dot blot chamber under vacuum. DNA was cross-linked to the membrane by exposure to UV light, dried at room temperature and prehybridized in 20 mM sodium phosphate, pH 7.5, containing 50% formamide, 5× SSC, 5× Denhardt's solution, 0.1% SDS and 100 μg/ml denatured yeast RNA at 42° C. for at least 3 hours. A 3.1 kilobase $^{32}$P-labeled β-galactosidase cDNA probe (0.3–1.0×10$^9$ cpm/μg) was hybridized to the filters with constant shaking for at least 16 hours at 42° C. Membranes were washed twice in 2× SSC and 0.1% SDS for 10 min each at 42° C., twice in 1× SSC and 0.1% SDS for 30 min each at 42° C., and once in 0.5× SSC and 0.1% SDS for 15 min at 55° C. prior to autoradiography.

Figure 2:
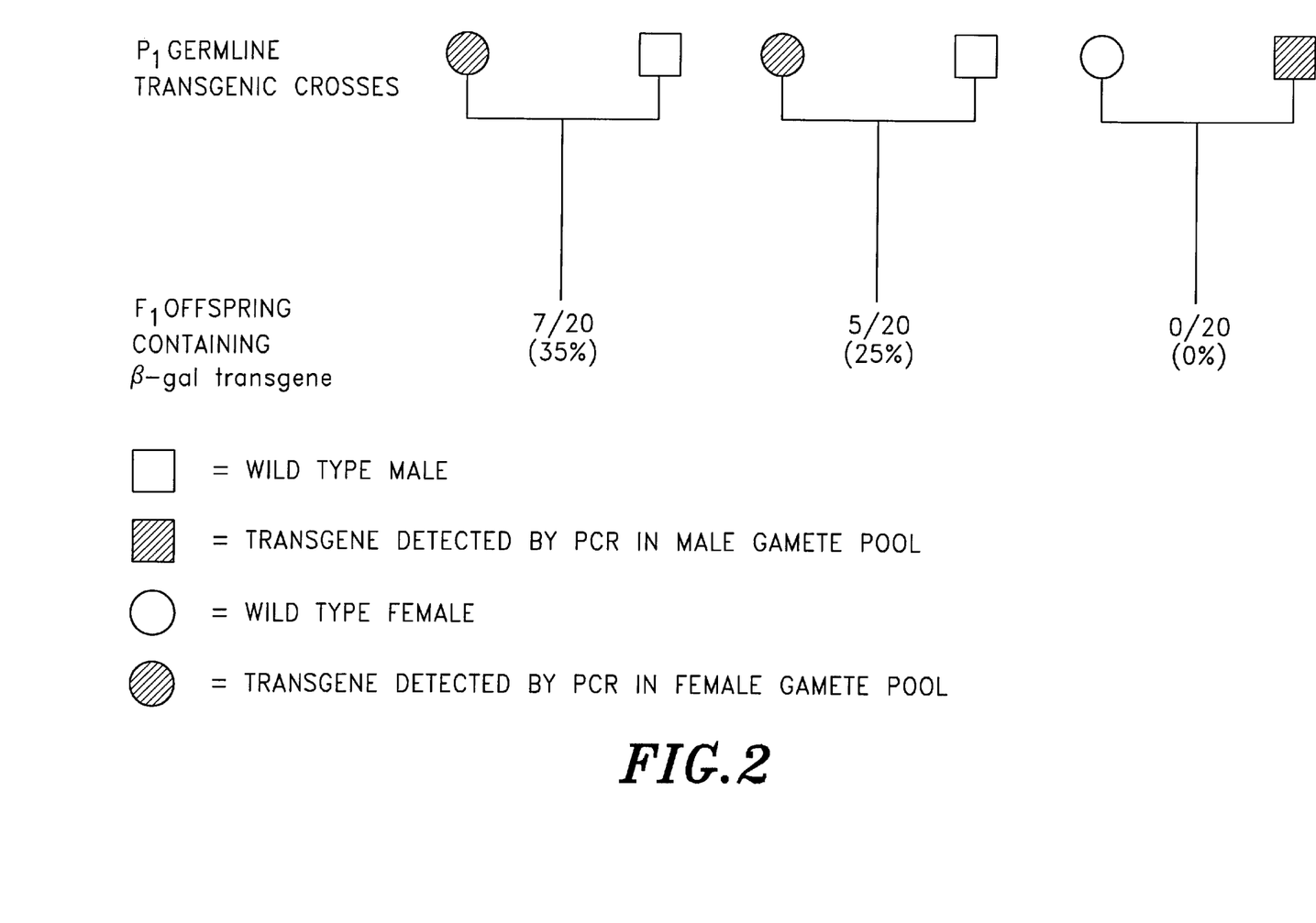
FIG. 2 is a schematic diagram showing the $P_1$ germline transgenic crosses and the percentage of $F_1$ offspring containing the β-galactosidase transgene.

From the crosses of the two female germline transgenic surfclams with wild type males, 7/20 (35%) and 5/20 (25%) of randomly selected F$_1$ offspring carried the β-galactosidase transgene (FIG. 2). A cross of the germline transgenic male with a wild type female yielded no transgenic F$_1$ progeny among the 20 offspring screened. These results suggest that the germlines of all 3 P$_1$ individuals were mosaic for the provirus.

Genomic DNA from two transgenic F$_1$ surfclams positive for the transgene by dot blot analysis was subjected to restriction endonuclease digestion and Southern hybridization to determine whether the provirus was integrated into the host genome or maintained as an extrachromosomal element. Genomic DNA (25 μg) was digested with Kpnl or EcoRV, resolved on an 0.8% agarose gel and transferred to a nylon membrane. Prehybridization and hybridization were carried out as described above. Digestion with Kpnl, which releases the full length 4.5 kb provirus, yielded a single band of the predicted size from each F$_1$ progeny when hybridized to a 3.1 kb β-galactosidase probe. Digestion of the F$_1$ clam DNA with EcoRV, which cuts once in the β-galactosidase coding sequence, and Pvull, which does not cut within the provirus, yielded two fragments of varying length from each of the F$_1$ surfclams when hybridized to a full length probe that should bind to both EcoRV fragments. If the provirus was episomally maintained, digestion fragments of approximately 2.0 and 2.5 kb would result from both the digestion with EcoRV and Pvull as well as with Pvull alone, and the hybridization pattern would be the same for each surfclam. The observation of much larger fragments that differed between surfclams suggests that host flanking sequence is contained in each of these hybridized fragments and that they are integrated into unique sites in the host genome. In addition, the appearance of only two bands from each clam with EcoRV and Pvull digestion and only a single band with Pvull alone suggests integration of a single provirus per clam genome.

To test for β-galactosidase expression mediated by the RSV LTR, the two P$_1$ females with mosaic germlines were bred to wild type males and batches of 5,000 F$_1$ progeny embryos were stained for β-galactosidase. Experimental and control F$_1$ embryos were fixed at 2–3 days post-fertilization in 1.25% glutaraldehyde in PBS (pH 8.2) for 10 min at room temperature. The fixed embryos were incubated in 0.6 mM chloroquine at 30° C. for 45 min to inhibit endogenous lysosomal β-galactosidase activity. After 2–3 washes in PBS, embryos were stained for 10–12 hours at 37° C. in a solution containing 1.2 mM X-gal, 0.1% Triton X-100, 1 mM MgCl$_2$, 0.01% sodium deoxycholate, 6 mM potassium ferricyanate and 6 mm potassium ferrocyanate. The stained embryos were then incubated in 1 mM phenylethyl-β-D-thiogalactopyranoside (PETG) to stop the staining reaction. Embryos were examined for blue color, indicating the presence of β-galactosidase, by light microscopy using an Olympus AH2 microscope.

A total of 500 trochophore-stage embryos from each cross were analyzed and an average of 24.0% and 33.4% of embryos from the two crosses, respectively, showed definite blue staining. Staining persisted into the late veliger stage 60–72 hours post-fertilization. No comparable blue staining was seen in the 500 control embryos.

EXAMPLE 6

Transfection of Surfclams with Genes of Interest

Plasmid pLNRCL in which "L" is the MoMLV LTR, "R" is an internal RSV promoter driving expression of cecropin gene C (Boman et al., ibid.) and N is the neomycin phosphotransferase gene is generated by standard molecular cloning techniques. This plasmid can be produced by inserting the cecropin gene under the control of the internal RSV promoter into plasmid pLNL, which can be derived from pLSRNL. Of course, the use of other retroviral long terminal repeats (LTRs), selectable markers, promoters and exogenous genes in the instant retroviral plasmid constructs for generation of VSV G pseudotyped retroviral vectors containing a gene of interest is also within the scope of the invention. LNRCL(VSV G) pseudotyped retroviral vectors are generated as described in Example 2. Surfclam embryos are infected with the pseudotyped retroviral vector as described in Example 4 and allowed to mature to adulthood. Gametes from resultant P1 individuals test positive for the presence of the cecropin gene by Southern blotting using a 32P-labeled fragment of the cecropin cDNA, indicating that the gene has been transferred to the germline. The P1 individuals will be more disease resistant than will those derived from nontransgenic embryos.

Genes encoding other invertebrate defense proteins contemplated for insertion into VSV G pseudotyped retroviral vectors include attacins, diptericins, and magainins. These genes can also be introduced into the germline of other mollusks using the same procedures described in the foregoing examples.

Genes encoding growth-accelerating hormones such as insulin-like growth factors (IGFs) and growth hormones (GHs) may also be inserted into the pseudotyped VSV G retroviral vectors. For example, the trout growth hormone gene may be inserted into the retroviral plasmid to generate pLNRGHL prior to generation of pseudotyped vector. Surfclam embryos are infected with the pseudotyped retroviral vector as described in Example 4 and allowed to mature to adulthood. Gametes from resultant P1 individuals test positive for the presence of the growth hormone gene by Southern blotting using a $^{32}$P-labeled fragment of the growth hormone cDNA, indicating that the gene has been transferred to the germline. The P1 individuals will grow faster and become larger than adults developing from untransfected embryos.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method for introducing exogenous DNA into a germline of a marine mollusk, comprising the steps of:

inserting said exogenous DNA into a plasmid comprising a promoter that is active in mollusks and retroviral long terminal repeats (LTRs), wherein said exogenous DNA is operably linked to said promoter, thereby generating a recombinant vector;

forming a pseudotyped retrovirus containing VSV G protein and RNA corresponding to said recombinant vector; and infecting a mollusk embryo with said pseudotyped retrovirus so as to insert said exogenous DNA into the germline of said mollusk.

2. The method of claim 1, wherein said marine mollusk is a clam.

3. The method of claim 1, wherein said marine mollusk is selected from the group consisting of oyster, mussel, scallop and abalone.

4. The method of claim 1, wherein said retroviral long terminal repeats are Moloney murine leukemia virus long terminal repeats.

5. The method of claim 1, wherein said infecting step is performed by electroporation.

6. The method of claim 1, wherein said infecting step is performed by dechorionation or microinjection.

7. The method of claim 1, wherein the inserting step comprises inserting said exogenous DNA into a first plasmid containing retroviral long terminal repeats, a gene encoding a selectable marker, and said promoter is operably linked to said exogenous DNA.

8. The method of claim 7, wherein the forming step comprises:

transfecting a packaging cell line with said first plasmid, wherein said cell line assembles vector particles containing an RNA copy of said recombinant vector;

infecting a producer cell line with said vector particles, said producer cell line containing retroviral gag and pol;

transfecting said vector particle-containing producer cell line with a second plasmid containing a promoter operably linked to VSV G protein, whereby pseudotyped retroviral vectors containing the VSV-G protein are secreted by said producer cell line.

9. The method of claim 7, wherein said first plasmid is pLSRNL or pGeo4.8.

10. The method of claim 7, wherein said promoter is the Rous sarcoma virus promoter.

11. The method of claim 7, wherein said selectable marker is neomycin phosphotransferase.

12. The method of claim 8, wherein said packaging cell line is PA317.

13. The method of claim 8, wherein said producer cell line is 293 cells.

14. The method of claim 8, wherein said second plasmid is pHCMV-G.

15. The method of claim 8, wherein said promoter of said second plasmid is cytomegalovirus promoter.

* * * * *

UNITED STATES PATENT AND TRADEMARK OFFICE
CERTIFICATE OF CORRECTION

PATENT NO.    : 5,969,211  
DATED         : October 19, 1999  
INVENTOR(S)   : Jane C. Burns and Thomas T. Chen It is certified that error appears in the above-identified patent and that said Letters Patent is hereby corrected as shown below:

Column 1,
Lines 9-13, please delete the paragraph in the specification and replace it with the following:

-- This invention was made with Government support under Sea Grant No. NA 36RG0537, awarded by the National Oceanic and Atmospheric Administration and Grant No. IBM 937132 awarded by the National Science Foundation. The government has certain rights in this invention --

Column 11,
Line 5, please delete "a promoter that is active in mollusks and"
Line 31, please delete "said promoter" and replace it with -- an internal promoter, whereby said exogenous DNA --
Line 32, please delete "exogenous DNA" and replace it with -- said promoter --.

Signed and Sealed this

Third Day of September, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 5,969,211                                    Page 1 of 1
DATED         : October 19, 1999
INVENTOR(S)   : Jane C. Burns and Thomas T. Chen It is certified that error appears in the above-identified patent and that said Letters Patent is hereby corrected as shown below:

Column 11,
Line 5, please add -- a promoter that is active in mollusks and --
Line 31, please delete "an internal promoter, whereby said exogenous DNA is operably linked to"

Signed and Sealed this

Second Day of December, 2003

JAMES E. ROGAN
*Director of the United States Patent and Trademark Office*

```
                         SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

GCATTGCATC AGCCATGA                                                          18

(2) INFORMATION FOR SEQ ID NO:2:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

GATGGATTGC ACGCAGGTTC                                                        20
```